US011274141B2

(12) United States Patent
Luo et al.

(10) Patent No.: US 11,274,141 B2
(45) Date of Patent: Mar. 15, 2022

(54) ENVELOPED VIRUS RESISTANT TO COMPLEMENT INACTIVATION FOR THE TREATMENT OF CANCER

(71) Applicant: Wellstat ImmunoTherapeutics, LLC, Rockville, MD (US)

(72) Inventors: Tianci Luo, Fulton, MD (US); Rene Molina, Hagerstown, MD (US); Gabriel Castille, Germantown, MD (US)

(73) Assignee: Wellstat ImmunoTherapeutics, LLC, Rockville, MD (US)

(*) Notice: Subject to any disclaimer, the term of this patent is extended or adjusted under 35 U.S.C. 154(b) by 615 days.

(21) Appl. No.: 16/303,729

(22) PCT Filed: May 10, 2018

(86) PCT No.: PCT/US2018/032018
§ 371 (c)(1),
(2) Date: Nov. 21, 2018

(87) PCT Pub. No.: WO2018/209052
PCT Pub. Date: Nov. 15, 2018

(65) Prior Publication Data
US 2019/0194292 A1 Jun. 27, 2019

Related U.S. Application Data

(60) Provisional application No. 62/504,120, filed on May 10, 2017.

(51) Int. Cl.
| C07K 19/00 | (2006.01) |
| C07K 14/705 | (2006.01) |
| A61K 35/768 | (2015.01) |
| A61P 35/00 | (2006.01) |
| C12N 15/62 | (2006.01) |
| A61K 35/76 | (2015.01) |
| C12N 5/16 | (2006.01) |
| A61K 38/00 | (2006.01) |

(52) U.S. Cl.
CPC ........ C07K 14/70596 (2013.01); A61K 35/76 (2013.01); A61K 35/768 (2013.01); A61P 35/00 (2018.01); C07K 14/70517 (2013.01); C07K 19/00 (2013.01); C12N 5/16 (2013.01); C12N 15/625 (2013.01); A61K 38/00 (2013.01); C07K 2319/03 (2013.01); C07K 2319/036 (2013.01); C12N 2760/18132 (2013.01); C12N 2760/18152 (2013.01)

(58) Field of Classification Search
CPC ........ C07K 14/70595; C07K 14/70517; C07K 19/00; A61P 35/00; A61K 38/00; A61K 38/117

See application file for complete search history.

(56) References Cited

U.S. PATENT DOCUMENTS

| 5,374,548 A | 12/1994 | Caras |
| 6,475,756 B1 * | 11/2002 | Wirth .................. C07K 14/005 424/192.1 |
| 6,497,873 B1 | 12/2002 | Whitt et al. |
| 7,056,689 B1 | 6/2006 | Lorence et al. |
| 8,877,896 B2 | 11/2014 | Kumar-Singh et al. |
| 2015/0191741 A1 | 7/2015 | Bundock |
| 2016/0361360 A1 | 12/2016 | Chang et al. |

FOREIGN PATENT DOCUMENTS

| CA | 2678774 A1 | 9/2008 |
| JP | 2008061539 A | 3/2008 |
| WO | 1999/027121 A1 | 6/1999 |
| WO | 2000062735 A2 | 10/2000 |
| WO | 2004045520 A2 | 6/2004 |
| WO | 2008118258 A2 | 10/2008 |
| WO | 2012151468 A1 | 11/2012 |
| WO | 2016164305 A1 | 10/2016 |
| WO | 2016174407 A1 | 11/2016 |
| WO | 20170197525 A1 | 11/2017 |

OTHER PUBLICATIONS

Hansbrough et al. 1991; Expression of a liver fatty acid binding protein/human decay-accelerating factor/HLA-B44 chimeric gene in transgenic mice. Am. J. Physiol. 260 (Gastrointest. Live Physiol. 23): G929-G939.*
Tykocinski et al. 1988; Glycolipid reanchoring of T-lymphocyte surface antigen CD8 using the 3' end sequence of decay-accelerating factor's mRNA. Proc. Natl. Acad. Sci. 85:3555-3559.*
Ahmad et al. 2010; Domain swapping reveals complement control protein modules critical for imparting cofactor rand decay-accelerating activities in vaccinia virus complement control protein. J. Immunol. 185: 6128-6137.*
Harris et al. 1999; Molecular and functional analysis of mouse decay accelerating factor (CD55). Biochem. J. 341: 821-829.*
Bell, 2020. Oncolytic Virus Therapy. Cancer Research Institute on the web at www.cancerresearch.org/en-us/immunotherapy/treatment-types/oncolytic-virus-therapy. pp. 1-7.*
Guibinga et al., "Baculovirus GP64-Pseudotyped HIV-Based Lentivirus Vectors are Stabilized Against Complement Inactivation by Codisplay of Decay Accelerating Factor (DAF) or of a GP64-DAF Fusion Protein", Molecular Therapy (Apr. 2005) 11(4): 645-651.

(Continued)

*Primary Examiner* — Karen Cochrane Carlson
(74) *Attorney, Agent, or Firm* — Lewis J. Kreisler

(57) ABSTRACT

A recombinant fusion protein is disclosed. The fusion protein comprises: (a) a CD55 peptide sequence, (b) a linker sequence C-terminal to the CD55 sequence, (c) a transmembrane domain C-terminal to the linker sequence, and (d) an intracellular domain C-terminal to the transmembrane domain. The fusion protein does not contain a GPI anchor. The fusion protein can be expressed with an N-terminal secretory signal peptide, which is cleaved to yield the mature protein on the surface of a cell line or an enveloped virus. An oncolytic virus expressing the fusion protein is resistant to complement inactivation and can be used to treat cancer.

Figure 1:
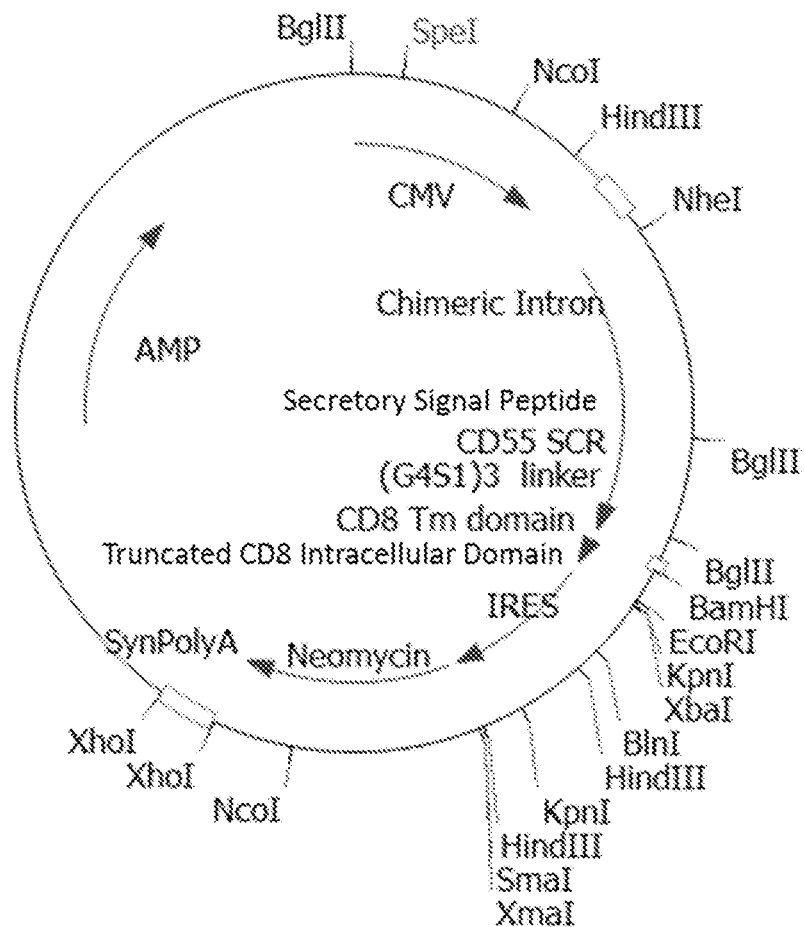
Figure 2:
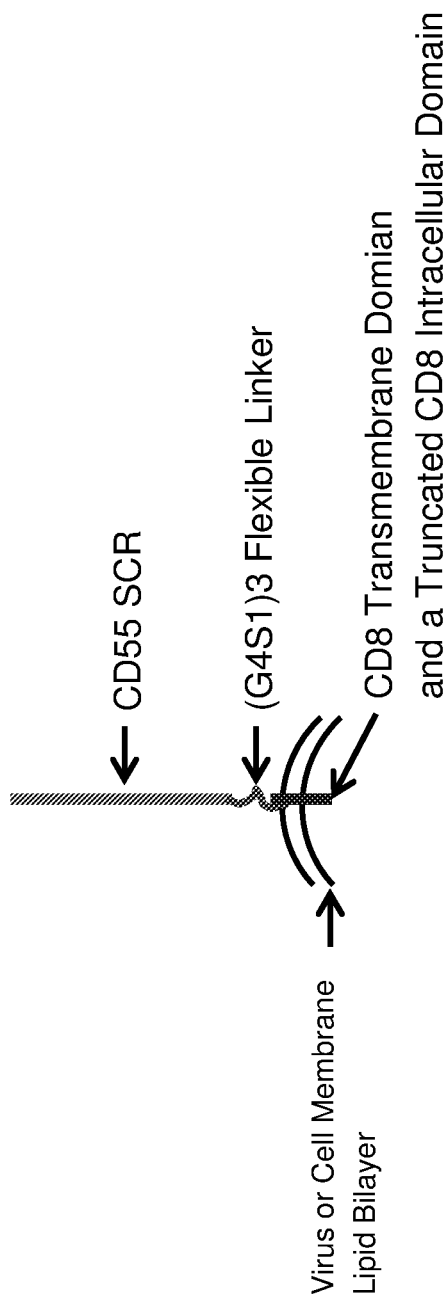

15 Claims, 5 Drawing Sheets
Specification includes a Sequence Listing.

(56) References Cited

OTHER PUBLICATIONS

Spitzer et al., "Complement-Protected Amphotropic Retroviruses from Murine Packaging Cells", Human Gene Therapy (Jul. 20, 1999) 10(11): 1893-1902.
Biswas et al., "Incorporation of host complement regulatory proteins into Newcastle Disease Virus enhances complement evasion", J. Virol. (Dec. 2012) 86(23): 12708-12716. Published ahead of print Sep. 12, 2012.
Rangaswamy et al., "CD55 is a key complement regulatory protein that counteracts complement-mediated inactivation of newcastle disease virus", J. Gen. Virol. (2016) 97: 1765-1770. <DOI 10.1099/jgv.0.000498>.
Fajardo et al., "Oncolytic adenoviral delivery of an EGFR-targeting T cell engager improves antitumor efficacy", Cancer Res. (Jan. 31, 2017) 35 pages. <DOI: 10.1158/0008-5472.CAN-16-1708>.
Chen et al., "Proteomics analysis of the DF-1 chicken fibroblasts infected with avian reovirus strain S1133", PLOS One (Mar. 2014) 9(3) e92154, 10 pages. <DOI:10.1371/journal.pone.0092154>.
Zamarin et al., "Oncolytic Newcastle Disease Virus for cancer therapy: old challenges and new directions", NIH Publich Access Author Manuscript 37 pages, published in final form as: Future Microbiol. (Mar. 2012) 7(3): 347-367. <DOI:10.2217/fmb.12.4>.
Andrews et al., "Sequences beyond the cleavage site influence signal peptide function", J. Biol. Chem. (1988) 263(30): 15791-15798.
Choo et al., "Flanking signal and mature peptide residues influence signal peptide cleavage", BMC Bioinformatics (Dec. 12, 2008) 9 (Suppl. 12): S15, 11 pages.
Neto at al., "Skeletal muscle signal peptide optimization for enhancing propeptide or cytokine secretion", HHS Public Access Author manuscript 15 pages, published in final edited form as: J. Theor. Biol. (Nov. 21, 2016) 409: 11-17. <DOI:10.1016/j.jtbi.2016.08.036>.
Carroll et al., "Organization of the genes encoding complement receptors type 1 and 2, decay accelerating factor, and C4 binding protein in the RCA locus on human chromosome", J. Exp. Med. (Apr. 1988) 167:1271-1280.
Rey-Campos et al., "A physical map of the human regulator of complement activation gene cluster linking the complement genes CR1, CR2, DAF, and C4BP", J. Exp. Med. (Feb. 1988) 167: 664-669.
Laurie et al., "A phase 1 clinical study of intravenous administration of PV701, an oncolytic virus, using two-step desensitization", Clin. Cancer Res. (Apr. 2006) 12(8): 2555-2562.
Lublin et al., "Decay-accelerating factor: biochemistry, molecular biology, and function", Ann. Rev. Immunol. (1989) 7: 35-38.
Nakano et al., "Complete determination of disulfide bonds localized within the short consensus repeat units of Decay Accelerating Factor (CD55 antigen)", Biochimica et Biophysica Acta (1992) 1116: 235-240.
Censullo et al., "How GPI-anchored proteins turnover: or where do they go after arrival at the plasma membrane", Semin. Immunol (1994) 6: 81-88.
Censullo et al., "The fate of GPI-anchored molecules", Brazilian J. Med. Biol. Res. (1994) 27: 289-295.
Morgan et al., "Membrane proteins that protect against complement lysis", Springer Semin. Immunopathol. (1994) 15:369-396.
Turner, "PIG-tailed membrane proteins", Essays Biochem. (1994) 28: 113-127.
Kim et al., "Membrane complement regulatory proteins", Clin. Immunol. (2006) 118: 127-136.
Pecora et al., "Phase I trial of intravenous administration of PV701, an oncolytic virrus, in patients with advanced solid cancers", J. Clin. Oncol. (May 1, 2002) 20(9): 2251-2266.
Lorence et al., "Phase 1 clinical experience using intravenous administration of PV701, an oncolytic Newcastle Disease Virus", Current Cancer Drug Targets (2007) 7:157-167.
Selvarangan et al., "Role of Decay-Accelerating Factor Domains and Anchorage in Internalization of Dr-Fimbriated *Escherichia coli*", Infect Immun. (Mar. 2000). 68(3): 1391-1399.
Miyagawa et al., "Delta-Short Consensus Repay 4-Decay Accelerating Factor (DAF: CD55) Inhibits Complement-Mediated Cytolysis but Not NK Cell-Mediated Cytolysis", J. Immunol. (2004). 173(6): 3945-3952.
Chen et al., "Fusion Protein Linkers: Property, Design and Functionality", Adv Drug Deliv Rev. (Oct. 2013). 65(10): 1357-1369.
Maeda et al., "Engineering of Functional Chimeric Protein G-Vargula Luciferase", Analytical Biochem. (1997). 249(2): 147-152.
Berry et al., "Substitution of Cysteine for Selenocysteine in Type I Iodothyronine Deiodinase Reduces the Catalytic Efficiency of the Protein but Enhances its Translation", Endocrinology. (1992). 131(4): 1848-1852.
Wollmann et al., "Some Attenuated Variants of Vesicular Stomatitis Virus Show Enhanced Oncolytic Activity against Human Glioblastoma Cells relative to Normal Brain Cells", J. Virol. (Feb. 2010). 84(3): 1563-1573.

* cited by examiner

MTVARPSVPAALPLLGELPRLLLVLLCLPAVWGDCGLPPDVPNAQPALEGRTSFPEDTV
ITYKCEESFVKIPGEKDSVICLKGSQWSDIEEFCNRSCEVPTRLNSASLKQPYITQNYFP
VGTVVEYECRPGYRREPSLSPKLTCLQNLKWSTAVEFCKKKSCPNPGEIRNGQIDVPGGI
LFGATISFSCNTGYKLFGSTSSFCLISGSSVQWSDPLPECREIYCPAPPQIDNGIIQGER
DHYGYRQSVTYACNKGFTMIGEHSIYCTVNNDEGEWSGPPPECRGKSLTSKVPPTVQKPT
TVNVPTTEVSPTSQKTTTKTTTPNAQATRSTPVSRTTKHFHETTPNKGSGTTGGGGSGGG
GSGGGGSIYIWAPLAGTCGVLLLSLVITLYCNHRNRRRV    (SEQ ID NO:2)

Figure 5

SEQUENCE LISTING

<160> NUMBER OF SEQ ID NOS: 3

<210> SEQ ID NO 1
<211> LENGTH: 6606
<212> TYPE: DNA
<213> ORGANISM: Artificial Sequence
<220> FEATURE:
<223> OTHER INFORMATION: Mammalian cell expression construct.
<220> FEATURE:

```
<221> NAME/KEY: misc_feature
<222> LOCATION: (1064)..(1165)
<223> OTHER INFORMATION: Code for secretory signal peptide
<220> FEATURE:
<221> NAME/KEY: misc_feature
<222> LOCATION: (1166)..(2119)
<223> OTHER INFORMATION: Code for SCR of CD55
<220> FEATURE:
<221> NAME/KEY: misc_feature
<222> LOCATION: (2120)..(2164)
<223> OTHER INFORMATION: Code for (G4S1)3 linker
<220> FEATURE:
<221> NAME/KEY: misc_feature
<222> LOCATION: (2165)..(2227)
<223> OTHER INFORMATION: Code for CD8 transmembrane domain
<220> FEATURE:
<221> NAME/KEY: misc_feature
<222> LOCATION: (2228)..(2260)
<223> OTHER INFORMATION: Code for truncated CD8 intracellular domain

<400> SEQUENCE: 1
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat     300
agtaacgcca tagggactt tccattgacg tcaatgggtg gagtatttac ggtaaactgc     360
ccacttggca gtacatcaag tgtatcatat gccaagtccg cccctattg acgtcaatga     420 cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg ggatttcca gtctccacc ccattgacgt      600 caatgggagt ttgttttggc accaaaatca acgggacttt ccaaaatgtc gtaataaccc     660
cgccccgttg acgcaaatgg gcggtaggcg tgtacggtgg gaggtctata taagcagagc     720
tcgtttagtg aaccgtcaga tcactagaag ctttattgcg gtagtttatc acagttaaat     780
tgctaacgca gtcagtgctt ctgacacaac agtctcgaac ttaagctgca gaagttggtc     840
gtgaggcact gggcaggtaa gtatcaaggt tacaagacag gtttaaggag accaatagaa     900
actgggcttg tcgagacaga gaagactctt gcgtttctga taggcaccta ttggtcttac     960
tgacatccac tttgcctttc tctccacagg tgtccactcc cagttcaatt acagctctta    1020
aggctagagt acttaatacg actcactata ggctagcgcc accatgacag tggccagacc    1080
ttctgtgcct gccgccctgc ctctgctggg agaactgcct agactgctgc tgctggtgct    1140
gctgtgtctg cctgccgtgt ggggcgattg tggcctgcct cccgatgtgc ctaatgccca    1200
gcctgccctg gaaggcagaa ccagcttccc cgaggacacc gtgatcacct acaagtgcga    1260
ggaatccttc gtgaagatcc ccggcgagaa ggatagcgtg atcctgctga gggcagcca    1320 gtggagcgac atcgaagagt tctgcaacag atcctgcgag gtgcccaccc ggctgaatag    1380
cgcctctctg aagcagccct acatcaccca gaactacttc cctgtgggca cgtggtgga    1440 atacgagtgc agacccggct acagaagaga gccctccctg agccctaagc tgacctgcct    1500
gcagaacctg aagtggtcca cgccgtgga gttctgtaaa agaagtcct gccccaaccc    1560 tggcgagatc cggaacggcc agattgatgt gcctggcggc atcctgttcg gcgcacacat    1620
cagcttcagc tgcaacaccg gctacaagct gttcggcagc acctccagct tttgcctgat    1680
cagcggcagc agcgtgcagt ggagtgaccc tctgcctgag tgcagagaga tctactgccc    1740
```

```
tgcccccct  cagatcgaca  acggcatcat  tcagggcgag  cgggaccact  acggctacag   1800
gcagagcgtg  acctacgcct  gcaacaaggg  cttcaccatg  atcggcgagc  acagcatcta   1860
ctgcaccgtg  aacaacgacg  agggcgagtg  gagcggccca  cccctgagt   gtagaggcaa   1920 gagcctgacc  agcaaggtgc  ccccaccgt   gcagaaaccc  accaccgtga  atgtgcctac   1980
caccgaggtg  tccccaacca  gccagaaaac  aaccaccaag  accaccaccc  ccaacgccca   2040
ggccaccaga  tctaccccctg tgtccaggac  caccaagcac  ttccacgaga  caaccccctaa  2100 caagggcagc  ggcacaaccg  gtggcggagg  atctggcggc  ggaggaagcg  gaggggggagg  2160 atccatctat  atctgggccc  ctctggccgg  cacctgtggc  gtgctgctgc  tgtctctcgt   2220
gatcaccctg  tactgcaacc  accggaaccg  gcggagagtg  tgatgagaat  tcacgcgtgg   2280
tacctctaga  gtcgaccctc  tagggcggcc  aattccgccc  ctctccctcc  ccccccccta   2340
acgttactgg  ccgaagccgc  ttggaataag  gccggtgtgc  gtttgtctat  atgttattt    2400 ccaccatatt  gccgtctttt  ggcaatgtga  gggcccggaa  acctggccct  gtcttcttga   2460
cgagcattcc  tagggtgtctt tccctctcg   ccaaaggaat  gcaaggtctg  ttgaatgtcg   2520
tgaaggaagc agttcctctg  gaagcttctt  gaagacaaac  aacgtctgta  gcgacccttt   2580
gcaggcagcg  gaaccccca   cctggcgaca  ggtgcctctg  cggccaaaag  ccacgtgtat   2640
aagatacacc  tgcaaaggcg  gcacaacccc  agtgccacgt  tgtgagttgg  atagttgtgg   2700
aaagagtcaa  atggctctcc  tcaagcgtat  tcaacaaggg  gctgaaggat  gcccagaagg   2760
taccccattg  tatgggatct  gatctggggc  ctcggtgcac  atgctttaca  tgtgtttagt   2820
cgaggttaaa  aaaacgtcta  ggccccccga  accacgggga  cgtggttttc  ctttgaaaaa   2880
cacgatgata  agcttgccac  aacccgggat  aattcctgca  gccaatatgg  gatcggccat   2940
tgaacaagat  ggattgcacg  caggttctcc  ggccgcttgg  gtggagaggc  tattcggcta   3000
tgactgggca  caacagacaa  tcggctgctc  tgatgccgcc  gtgttccggc  tgtcagcgca   3060
ggggcgcccg  gttctttttg  tcaagaccga  cctgtccggt  gccctgaatg  aactgcagga   3120
cgaggcagcg  cggctatcgt  ggctggccac  gacgggcgtt  ccttgcgcag  ctgtgctcga   3180
cgttgtcact  gaagcgggaa  gggactggct  gctattgggc  gaagtgccgg  ggcaggatct   3240
cctgtcatct  caccttgctc  ctgccgagaa  agtatccatc  atggctgatg  caatgcggcg   3300
gctgcatacg  cttgatccgg  ctacctgccc  attcgaccac  caagcgaaac  atcgcatcga   3360
gcgagcacgt  actcggatgg  aagccggtct  tgtcgatcag  gatgatctgg  acgaagagca   3420 tcagggctc   cgccagccg   aactgttcgc  caggctcaag  gcgcgcatgc  ccgacggcga   3480
tgatctcgtc  gtgacccatg  gcgatgcctg  cttgccgaat  atcatggtgg  aaaatggccg   3540
cttttctgga  ttcatcgact  gtggccggct  gggtgtggcg  gaccgctatc  aggacatagc   3600
gttggctacc  cgtgatattg  ctgaagagct  tggcggcgaa  tgggctgacc  gcttcctcgt   3660
gctttacggt  atcgccgctc  ccgattcgca  gcgcatcgcc  ttctatcgcc  ttcttgacga   3720
gttcttctga  ggggatcaat  tctgggcggc  ctcgagaata  acaatcatt   attttcattg   3780 gatctgtgtg  ttggttttt   gtgtgggctt  ggggagggg   gaggccagaa  tgactccaag   3840
agctacagga  aggcaggtca  gagacccac   tggacaaaca  gtggctggac  tctgcaccat   3900
aacacacaat  caacagggga  gtgagctgga  tcgagctgct  cgagatccgg  gctggcgtaa   3960
tagcgaagag  gcccgcaccg  atcgcccttc  ccaacagttg  cgcagcctga  atggcgaatg   4020
gacgcgccct  gtagcggcgc  attaagcgcg  gcgggtgtgg  tggttacgcg  cagcgtgacc   4080
```

```
gctacacttg ccagcgccct agcgcccgct cctttcgctt tcttcccttc ctttctcgcc    4140
acgttcgccg gctttccccg tcaagctcta aatcggggc  tccctttagg gttccgattt    4200
agtgctttac ggcacctcga ccccaaaaaa cttgattagg gtgatggttc acgtagtggg    4260
ccatcgccct gatagacggt ttttcgccct ttgacgttgg agtccacgtt ctttaatagt    4320
ggactcttgt tccaaactgg aacaacactc aaccctatct cggtctattc ttttgattta    4380
taagggattt tgccgatttc ggcctattgg ttaaaaaatg agctgattta acaaaaattt    4440
aacgcgaatt ttaacaaaat attaacgctt acaatttcct gatgcggtat tttctcctta    4500
cgcatctgtg cggtatttca caccgcatat ggtgcactct cagtacaatc tgctctgatg    4560
ccgcatagtt aagccagccc cgacacccgc caacacccgc tgacgcgccc tgacgggctt    4620
gtctgctccc ggcatccgct tacagacaag ctgtgaccgt ctccgggagc tgcatgtgtc    4680
agaggttttc accgtcatca ccgaaacgcg cgagacgaaa gggcctcgtg atacgcctat    4740
ttttataggt taatgtcatg ataataatgg tttcttagac gtcaggtggc acttttcggg    4800
gaaatgtgcg cggaacccct atttgtttat ttttctaaat acattcaaat atgtatccgc    4860
tcatgagaca ataaccctga taaatgcttc aataatattg aaaaaggaag agtatgagta    4920
ttcaacattt ccgtgtcgcc cttattccct ttttgcggc  attttgcctt cctgtttttg    4980
ctcacccaga aacgctggtg aaagtaaaag atgctgaaga tcagttgggt gcacgagtgg    5040
gttacatcga actggatctc aacagcggta agatccttga gagttttcgc cccgaagaac    5100
gttttccaat gatgagcact tttaaagttc tgctatgtgg cgcggtatta tcccgtattg    5160
acgccgggca agagcaactc ggtcgccgca tacactattc tcagaatgac ttggttgagt    5220
actcaccagt cacagaaaag catcttacgg atggcatgac agtaagagaa ttatgcagtg    5280
ctgccataac catgagtgat aacactgcgg ccaacttact tctgacaacg atcggaggac    5340
cgaaggagct aaccgctttt ttgcacaaca tgggggatca tgtaactcgc cttgatcgtt    5400
gggaaccgga gctgaatgaa gccataccaa acgacgagcg tgacaccacg atgcctgtag    5460
caatggcaac aacgttgcgc aaactattaa ctggcgaact acttactcta gcttcccggc    5520
aacaattaat agactggatg gaggcggata aagttgcagg accacttctg cgctcggccc    5580
ttccggctgg ctggtttatt gctgataaat ctggagccgg tgagcgtggg tctcgcggta    5640
tcattgcagc actggggcca gatggtaagc cctcccgtat cgtagttatc tacacgacgg    5700
ggagtcaggc aactatggat gaacgaaata gacagatcgc tgagataggt gcctcactga    5760
ttaagcattg gtaactgtca gaccaagttt actcatatat actttagatt gatttaaaac    5820
ttcatttta atttaaaagg atctaggtga agatcctttt tgataatctc atgaccaaaa    5880
tcccttaacg tgagttttcg ttccactgag cgtcagaccc cgtagaaaag atcaaaggat    5940
cttcttgaga tcctttttt  ctgcgcgtaa tctgctgctt gcaaacaaaa aaaccaccgc    6000
taccagcggt ggtttgtttg ccggatcaag agctaccaac tctttttccg aaggtaactg    6060
gcttcagcag agcgcagata ccaaatactg ttcttctagt gtagccgtag ttaggccacc    6120
acttcaagaa ctctgtagca ccgcctacat acctcgctct gctaatcctg ttaccagtgg    6180
ctgctgccag tggcgataag tcgtgtctta ccgggttgga ctcaagacga tagttaccgg    6240
ataaggcgca gcggtcgggc tgaacggggg gttcgtgcac acagcccagc ttggagcgaa    6300
cgacctacac cgaactgaga tacctacagc gtgagctatg agaaagcgcc acgcttcccg    6360
aagggagaaa ggcggacagg tatccggtaa gcggcagggt cggaacagga gagcgcacga    6420
gggagcttcc agggggaaac gcctggtatc tttatagtcc tgtcgggttt cgccacctct    6480
```

-continued

```
gacttgagcg tcgattttg tgatgctcgt caggggggcg gagcctatgg aaaaacgcca    6540
gcaacgcggc cttttacgg ttcctggcct tttgctggcc ttttgctcac atggctcgac    6600
agatct                                                              6606
```

<210> SEQ ID NO 2
<211> LENGTH: 399
<212> TYPE: PRT
<213> ORGANISM: Artificial Sequence
<220> FEATURE:
<223> OTHER INFORMATION: Fusion protein
<220> FEATURE:
<221> NAME/KEY: SIGNAL
<222> LOCATION: (1)..(34)
<223> OTHER INFORMATION: Secretory signal peptide
<220> FEATURE:
<221> NAME/KEY: PEPTIDE
<222> LOCATION: (35)..(352)
<223> OTHER INFORMATION: SCR of CD55
<220> FEATURE:
<221> NAME/KEY: MISC_FEATURE
<222> LOCATION: (353)..(367)
<223> OTHER INFORMATION: (G4S1)3 linker
<220> FEATURE:
<221> NAME/KEY: TRANSMEM
<222> LOCATION: (368)..(388)
<223> OTHER INFORMATION: CD8 transmembrane domain
<220> FEATURE:
<221> NAME/KEY: DOMAIN
<222> LOCATION: (389)..(399)
<223> OTHER INFORMATION: Truncated CD8 intracellular domain

<400> SEQUENCE: 2

Met Thr Val Ala Arg Pro Ser Val Pro Ala Ala Leu Pro Leu Leu Gly
1               5                   10                  15

Glu Leu Pro Arg Leu Leu Leu Leu Val Leu Leu Cys Leu Pro Ala Val
            20                  25                  30

Trp Gly Asp Cys Gly Leu Pro Pro Asp Val Pro Asn Ala Gln Pro Ala
        35                  40                  45

Leu Glu Gly Arg Thr Ser Phe Pro Glu Asp Thr Val Ile Thr Tyr Lys
    50                  55                  60

Cys Glu Glu Ser Phe Val Lys Ile Pro Gly Glu Lys Asp Ser Val Ile
65                  70                  75                  80

Cys Leu Lys Gly Ser Gln Trp Ser Asp Ile Glu Glu Phe Cys Asn Arg
                85                  90                  95

Ser Cys Glu Val Pro Thr Arg Leu Asn Ser Ala Ser Leu Lys Gln Pro
            100                 105                 110

Tyr Ile Thr Gln Asn Tyr Phe Pro Val Gly Thr Val Val Glu Tyr Glu
        115                 120                 125

Cys Arg Pro Gly Tyr Arg Arg Glu Pro Ser Leu Ser Pro Lys Leu Thr
    130                 135                 140

Cys Leu Gln Asn Leu Lys Trp Ser Thr Ala Val Glu Phe Cys Lys Lys
145                 150                 155                 160

Lys Ser Cys Pro Asn Pro Gly Glu Ile Arg Asn Gly Gln Ile Asp Val
                165                 170                 175

Pro Gly Gly Ile Leu Phe Gly Ala Thr Ile Ser Phe Ser Cys Asn Thr
            180                 185                 190

Gly Tyr Lys Leu Phe Gly Ser Thr Ser Ser Phe Cys Leu Ile Ser Gly
        195                 200                 205

Ser Ser Val Gln Trp Ser Asp Pro Leu Pro Glu Cys Arg Glu Ile Tyr
    210                 215                 220

```
Cys Pro Ala Pro Pro Gln Ile Asp Asn Gly Ile Gln Gly Glu Arg
225                 230                 235                 240

Asp His Tyr Gly Tyr Arg Gln Ser Val Thr Tyr Ala Cys Asn Lys Gly
            245                 250                 255

Phe Thr Met Ile Gly Glu His Ser Ile Tyr Cys Thr Val Asn Asn Asp
            260                 265                 270

Glu Gly Glu Trp Ser Gly Pro Pro Glu Cys Arg Gly Lys Ser Leu
        275                 280                 285

Thr Ser Lys Val Pro Pro Thr Val Gln Lys Pro Thr Thr Val Asn Val
    290                 295                 300

Pro Thr Thr Glu Val Ser Pro Thr Ser Gln Lys Thr Thr Thr Lys Thr
305                 310                 315                 320

Thr Thr Pro Asn Ala Gln Ala Thr Arg Ser Thr Pro Val Ser Arg Thr
            325                 330                 335

Thr Lys His Phe His Glu Thr Thr Pro Asn Lys Gly Ser Gly Thr Thr
            340                 345                 350

Gly Gly Gly Gly Ser Gly Gly Gly Gly Ser Gly Gly Gly Gly Ser Ile
            355                 360                 365

Tyr Ile Trp Ala Pro Leu Ala Gly Thr Cys Gly Val Leu Leu Leu Ser
370                 375                 380

Leu Val Ile Thr Leu Tyr Cys Asn His Arg Asn Arg Arg Arg Val
385                 390                 395

<210> SEQ ID NO 3
<211> LENGTH: 365
<212> TYPE: PRT
<213> ORGANISM: Artificial Sequence
<220> FEATURE:
<223> OTHER INFORMATION: Mature fusion protein (after cleavage of signal
      peptide).
<220> FEATURE:
<221> NAME/KEY: PEPTIDE
<222> LOCATION: (1)..(318)
<223> OTHER INFORMATION: SCR of CD55
<220> FEATURE:
<221> NAME/KEY: MISC_FEATURE
<222> LOCATION: (319)..(333)
<223> OTHER INFORMATION: (G4S1)3 linker
<220> FEATURE:
<221> NAME/KEY: TRANSMEM
<222> LOCATION: (334)..(354)
<223> OTHER INFORMATION: CD8 transmembrane domain
<220> FEATURE:
<221> NAME/KEY: DOMAIN
<222> LOCATION: (355)..(365)
<223> OTHER INFORMATION: Trunated CD8 intracellular domain

<400> SEQUENCE: 3

Asp Cys Gly Leu Pro Pro Asp Val Pro Asn Ala Gln Pro Ala Leu Glu
1               5                   10                  15

Gly Arg Thr Ser Phe Pro Glu Asp Thr Val Ile Thr Tyr Lys Cys Glu
            20                  25                  30

Glu Ser Phe Val Lys Ile Pro Gly Glu Lys Asp Ser Val Ile Cys Leu
        35                  40                  45

Lys Gly Ser Gln Trp Ser Asp Ile Glu Glu Phe Cys Asn Arg Ser Cys
    50                  55                  60

Glu Val Pro Thr Arg Leu Asn Ser Ala Ser Leu Lys Gln Pro Tyr Ile
65                  70                  75                  80

Thr Gln Asn Tyr Phe Pro Val Gly Thr Val Val Glu Tyr Glu Cys Arg
                85                  90                  95

Pro Gly Tyr Arg Arg Glu Pro Ser Leu Ser Pro Lys Leu Thr Cys Leu
```

-continued

```
                100                  105                    110
Gln Asn Leu Lys Trp Ser Thr Ala Val Glu Phe Cys Lys Lys Ser
        115                     120                 125

Cys Pro Asn Pro Gly Glu Ile Arg Asn Gly Gln Ile Asp Val Pro Gly
        130                     135                 140

Gly Ile Leu Phe Gly Ala Thr Ile Ser Phe Ser Cys Asn Thr Gly Tyr
145                     150                     155                 160

Lys Leu Phe Gly Ser Thr Ser Ser Phe Cys Leu Ile Ser Gly Ser Ser
                    165                     170                 175

Val Gln Trp Ser Asp Pro Leu Pro Glu Cys Arg Glu Ile Tyr Cys Pro
                180                     185                 190

Ala Pro Pro Gln Ile Asp Asn Gly Ile Ile Gln Gly Glu Arg Asp His
        195                     200                 205

Tyr Gly Tyr Arg Gln Ser Val Thr Tyr Ala Cys Asn Lys Gly Phe Thr
        210                     215                 220

Met Ile Gly Glu His Ser Ile Tyr Cys Thr Val Asn Asn Asp Glu Gly
225                     230                     235                 240

Glu Trp Ser Gly Pro Pro Glu Cys Arg Gly Lys Ser Leu Thr Ser
                    245                     250                 255

Lys Val Pro Pro Thr Val Gln Lys Pro Thr Thr Val Asn Val Pro Thr
                260                     265                 270

Thr Glu Val Ser Pro Thr Ser Gln Lys Thr Thr Thr Lys Thr Thr Thr
                275                     280                 285

Pro Asn Ala Gln Ala Thr Arg Ser Thr Pro Val Ser Arg Thr Thr Lys
        290                     295                 300

His Phe His Glu Thr Thr Pro Asn Lys Gly Ser Gly Thr Thr Gly Gly
305                     310                     315                 320

Gly Gly Ser Gly Gly Gly Gly Ser Gly Gly Gly Gly Ser Ile Tyr Ile
                    325                     330                 335

Trp Ala Pro Leu Ala Gly Thr Cys Gly Val Leu Leu Leu Ser Leu Val
                340                     345                 350

Ile Thr Leu Tyr Cys Asn His Arg Asn Arg Arg Val
        355                     360                 365
```

ENVELOPED VIRUS RESISTANT TO COMPLEMENT INACTIVATION FOR THE TREATMENT OF CANCER

REFERENCE TO SEQUENCE LISTING

The Sequence Listing filed electronically in the form of an Annex C/ST.25 text file and bearing file reference 21003-PCT is a part of the disclosure.

BACKGROUND OF THE INVENTION

Oncolytic viruses have been tested as agents for the treatment of cancers by infecting and destroying tumor cells. These oncolytic viruses include Newcastle Disease Virus, Adenovirus, Sindbis virus, Vaccinia virus, Herpes virus etc. Newcastle Disease Virus (NDV) showed a great potential in shrinking tumor in cancer patients due to its unique property of preferential replication in and lysis of tumor cells, presumably owing to the factor that most tumor cells have a deficient interferon pathway (Pecora et al., 2002; Laurie et al., 2006; Lorence et al., 2007). Despite the preliminary promising clinical results, NDV as a cancer therapeutic agent has a shortcoming: inevitably most of the NDV particles will be destroyed by the patient's innate immune system, the alternative complement pathway, once the viruses enter the patient's body.

The complement system is a part of the innate and adaptive immune system (reviewed by Volanakis, J. E., 1998. Chapter 2. In *The Human Complement System in Health and Disease*. Edited by J. E. Volanakis, and M. M. Frank. Marcel Dekker, Inc., New York pp 9-32). Complement plays an important role in microbial killing, and for the transport and clearance of immune complexes. Many of the activation products of the complement system are also associated with proinflammatory or immunoregulatory functions. The complement system consists of plasma and membrane-associated proteins that are organized in three enzymatic-activation cascades: the classical, the lectin, and the alternative pathways. All three pathways can lead to the formation of the terminal complement complex/membrane attack complex (TCC/MAC) and an array of biologically active products.

Human cells and organs have a family of membrane-bound complement regulatory proteins to protect them from homologous complement-mediated lysis. These complement regulatory proteins include CD55 (decay-accelerating factor, DAF), CD46 (membrane cofactor protein, MCP), CD35 (complement receptor 1, CR1), and CD59 (membrane inhibitor of reactive lysis) (Carroll et al., 1988; Rey-Campos et al., 1988; Lublin et al., 1989; Morgan et al., 1994; Kim and Song, 2006).

CD55 is a glycosylphosphatidylinositol (GPI)-anchored protein and attaches to a cell plasma membrane through a glycolipid moiety (GPI anchor) at its C-terminus. The GPI-anchored proteins such as CD55 can be endocytosed and degraded or cleaved and released from cell plasma membrane (Censullo and Davitz, 1994a, 1994b; Turner 1994). For example, The GPI-anchored proteins including CD55 can be released from the cell surface by the action of GPI-specific phospholipases C and D (Turner 1994). These enzymatic activities likely control the catabolism of GPI-anchored proteins and regulate the cell surface expression of these proteins (Censullo and Davitz, 1994b).

SUMMARY OF THE INVENTION

This invention provides a recombinant fusion protein comprising: (a) a CD55 peptide sequence, (b) a linker sequence C-terminal to the CD55 sequence, (c) a transmembrane domain C-terminal to the linker sequence, and (d) an intracellular domain C-terminal to the transmembrane domain, wherein the fusion protein does not contain a GPI anchor. This invention also provides nucleic acids and expression vectors encoding the protein, cells expressing the protein, enveloped viruses incorporating the protein on the viral membrane, pharmaceutical compositions comprising the protein-incorporating virus of this invention, as well as methods of treatment and uses of the virus.

This invention is based, in part, on the finding that virus expressing a fusion protein according to this invention was resistant to inactivation by normal human serum, as evidenced by a higher recovery rate compared to virus not expressing the fusion protein. The oncolytic enveloped virus produced by the engineered cells of the invention which incorporate complement inhibitor in the form of a recombinant fusion protein on the viral membrane is a better cancer therapeutic and affords better clinical outcomes for cancer patients as compared to the corresponding virus lacking a complement inhibitor on the viral membrane, due to its survival capability in the human serum circulation before it gets into a tumor. The benefits are three-fold: 1) the oncolytic virus can be produced in a cell culturing system in a bio-reactor; 2) fewer viral particles are needed to achieve the same therapeutic efficacy as compared to the parental oncolytic virus produced in chicken eggs; 3) infusion of fewer viral particles to a cancer patient may reduce side effects associated with large amounts of viral particles such as cytokine storm or impurity related effects.

Others who have studied the effects of the complement regulatory protein CD55 on the protection of Newcastle Disease Virus (NDV) (Biswas et al., 2012; Rangaswamy et al., 2016) used native unmodified CD55, which includes a glycosylphosphatidyl-inositol (GPI) anchor. In contrast the fusion protein of this invention omits the GPI anchor. Without wishing to be bound by theory it is believed that the omission of a GPI anchor changed the catabolism dynamics of CD55 on the cell surface. The fusion protein of this invention was able to withstand inactivation conditions more stringent than those utilized by Biswas and Rangaswamy. Biswas used 5 to 10% normal human serum and Rangaswamy used 0.3 to 5% normal human serum in their inactivation assays. The example below used 40% normal human serum to conduct the inactivation assay on NDV that has incorporated the recombinant fusion protein.

BRIEF DESCRIPTION OF THE FIGURES

FIG. 1. Mammalian cell expression construct map sequence encoding a recombinant complement inhibitory fusion protein consisting of a secretory signal peptide, four short consensus repeat (SCR) of CD55, a flexible linker, a CD8 transmembrane domain and a truncated CD8 intracellular domain, followed by IRES-neo selectable marker and a synthetic polyadenylation signal (polyA).

FIG. 2. Diagram illustrating the orientation of the matured complement inhibitory fusion protein on the engineered DF1 cell membrane or on modified NDV membrane.

FIG. 3. Cell surface expression of a recombinant complement inhibitory fusion protein. Flow cytometry analysis for the fusion protein expression by a CD55 specific antibody. The histogram on the left represents the naïve DF1 cells as a negative control. The histogram on the right represents the DF1 cells stably expressing SEQ ID NO:2 (cell clone number 8).

FIG. 4. Cytotoxicity assay of NDV produced by the engineered DF1 cells (Clone number 8) incorporated with the complement inhibitory fusion protein in tumor cell lines.

FIG. 5. Amino Acid Sequence of a recombinant complement inhibitory fusion protein consisting of secretory signal peptide, four short consensus repeat (SCR) of CD55, a flexible linker, a CD8 transmembrane domain and a truncated CD8 intracellular domain. (SEQ ID NO:2)
Double Underlined indicates Secretory signal peptide
Regular type indicates SCR of CD55
Underlined indicates (G4S1)3 Linker
Bold indicates the CD8 transmembrane domain
Italic indicates the truncated CD8 intracellular domain

DETAILED DESCRIPTION OF THE INVENTION

In accordance with the fusion protein of this invention any CD55 peptide sequence can be utilized for sequence (a). In an embodiment the CD55 peptide sequence is a human CD55 peptide sequence. The CD55 peptide sequence preferably comprises four short consensus repeats (SCR) of CD55. Any flexible linker can be utilized for sequence (b), for example a conventional flexible linker known in the field. In one embodiment a G4S1 linker is utilized, preferably a (G4S1)3 linker. Any transmembrane domain can be utilized for sequence (c), for example a conventional transmembrane domain known in the field. In one embodiment the transmembrane domain is a CD8 transmembrane domain. Any intracellular domain can be utilized for sequence (d), for example a conventional intracellular domain. In one embodiment the transmembrane domain is a CD8 transmembrane domain, preferably a truncated CD8 transmembrane domain.

The fusion protein of this invention can further comprise a secretory signal peptide N-terminal to sequence (a). In accordance with the preferred process of this invention the fusion protein is initially expressed with the signal peptide. The signal peptide directs the newly synthesized fusion protein to the endoplasmic reticulum (ER), where the signal peptide is cleaved by signal peptidase. SEQ ID NO:2 is an exemplary fusion protein of this invention having an N-terminal signal peptide. SEQ ID NO:3 is an exemplary fusion protein of this invention not having an N-terminal signal peptide.

In accordance with the fusion protein of this invention there can optionally be a spacer of one or more amino acids between the N-terminal signal peptide and sequence (a), between sequence (a) and sequence (b), between sequence (b) and sequence (c), between sequence (c) and sequence (d), between any two of them, between any three of them, or between all four. In one embodiment of this invention there is no spacer between the N-terminal signal peptide and sequence (a), or in other words the N-terminal signal peptide is covalently bonded to sequence (a) by a single peptide bond. In another embodiment there is a spacer between the N-terminal signal peptide and sequence (a).

In one embodiment of this invention there is no spacer between sequence (a) and sequence (b), or in other words sequence (a) is covalently bonded to sequence (b) by a single peptide bond. In another embodiment there is a spacer between sequence (a) and sequence (b). In one embodiment of this invention there is no spacer between sequence (b) and sequence (c), or in other words sequence (b) is covalently bonded to sequence (c) by a single peptide bond. In another embodiment there is a spacer between sequence (b) and sequence (c). In one embodiment of this invention there is no spacer between sequence (c) and sequence (d), or in other words sequence (c) is covalently bonded to sequence (d) by a single peptide bond. In another embodiment there is a spacer between sequence (c) and sequence (d). There is in principle no limitation on the size of the spacers.

CD55 contains four extracellular short consensus repeat (SCR), a Ser/Thr/Pro (STP)-rich region and a GPI-anchored domain. In accordance with the fusion protein of this invention the GPI-anchor domain is omitted. The STP-rich region can be present or absent. One embodiment of the fusion protein coding sequence of this invention further comprises a polyadenylation signal C-terminal to the third peptide sequence coding sequence. The polyadenylation signal (Poly A) can be any Poly A.

This invention provides a nucleic acid encoding the protein described above. In one embodiment the nucleic acid is DNA. It can optionally contain one or more introns, either between the sequences coding for the signal peptide and sequence (a), between sequence (a) and sequence (b), between sequence (b) and sequence (c), between sequence (c) and sequence (d), or elsewhere. In an embodiment of this invention the nucleic acid encodes a protein having the sequence SEQ ID NO:2 or SEQ ID NO:3. SEQ ID NO:1 is one example of a nucleic acid encoding a protein having the sequence SEQ ID NO:2. Because different nucleic acid codon triplets code for the same amino acid, a relationship known as the degeneracy of the genetic code, many other nucleic acid sequences that encode a protein having the sequence SEQ ID NO:2 can readily be envisioned and are included in this invention.

An embodiment of this invention is an expression vector comprising the nucleic acid described above operatively linked to a control sequence, for example a promoter. The promoter driving the fusion protein can be any promoter and is not limited to a CMV promoter. When there is an intron between the promoter and the fusion protein coding sequence, any suitable and conventional intron can be utilized. For example, a (3-globin intron is suitable.

This invention provides a cell line stably expressing the fusion protein of this invention on its cell surface. Any conventional cell line for protein expression can be used in accordance with this invention. In one embodiment the cell line is a mammalian cell line. In another embodiment the cell line is a non-mammalian cell line, for example a DF-1 chicken embryonic fibroblast cell line.

This invention provides an enveloped virus incorporating the fusion protein described above on the virus membrane. In accordance with this invention any enveloped virus can be utilized. In an embodiment the virus is an oncolytic virus, for example a paramyxovirus such as Newcastle Disease Virus (NDV). In the examples a complement inhibitor in the form of a recombinant fusion protein was incorporated onto NDV particles envelope. The recombinant fusion protein of this invention could be used for oncolytic viruses other than NDV, leading to generation of oncolytic viral particles that are more resistant to host complement inactivation. The novel recombinant complement inhibitor in the form of a fusion protein can be used to modify any other mammalian cells such as HeLa cells to produce oncolytic viruses. Oncolytic viruses are described in International Patent Publication No. WO 2000/062735, the content of which is incorporated by reference. In the experiments whose results are presented below the NDV utilized was PPMK107 described in WO 2000/062735.

The virus can be incorporated in a pharmaceutical composition that comprises the virus and a pharmaceutically acceptable carrier. This invention provides a method for treating a neoplastic condition in a mammalian subject, comprising administering to the subject an amount of the virus described above effective to treat the neoplastic condition. For cancer treatment the virus can be administrated to the patients via any conventional route, for example by one or more intratumoral or intravenous injections. For intratumoral administration, the dose range can be from $1\times10^7$ to $5\times10^{12}$ pfu/per tumor. For intravenous administration, the dose range can be from $1\times10^7$ to $1\times10^{13}$ pfu/m$^2$. ('Pfu' is an abbreviation for 'plaque forming unit'.)

The oncolytic virus according to this invention could also be engineered to incorporate other molecules such as GMCSF to enhance the efficacy of the oncolytic virus. In addition, the oncolytic virus could be a part of a combination cancer therapy with a checkpoint inhibitor such as anti-PD1 or anti-PDL1 molecule. Further, the oncolytic virus could be a part of a combination cancer therapy with other chemotherapeutic agents. The chemotherapeutic agents could be but are not limited to camptothecin compounds, for example, irinotecan or topotecan.

All publications, patents and patent applications mentioned in this specification are herein incorporated by reference in their entirety into the specification to the same extent as if each individual publication, patent or patent application was specifically and individually indicated to be incorporated herein by reference. Also incorporated by reference is any supplemental information that was published along with any of the aforementioned publications, patents and patent applications. For example, some journal articles are published with supplemental information that is typically available online.

The invention will be better understood by reference to the following examples, which illustrate but do not limit the invention described herein.

EXAMPLES

Example 1

A modified version of recombinant CD55 with a four short consensus repeat (SCR) of CD55 downstream of the secretory signal peptide followed by a flexible linker (3×G4S1) and a CD8 transmembrane and a truncated CD8 intracellular domain was created (FIG. 1). The coding sequence was cloned into a mammalian expression construct that has a CMV promoter, a synthetic intron driving the recombinant protein expression. The expression cassette also contained a drug selectable marker, neomycin phosphotransferase downstream from IRES. The gene expression cassette ended with a synthetic polyadenylation signal. SEQ ID NO:1 is the nucleotide sequence of the mammalian cell expression construct. SEQ ID NO:2 represents the amino acid sequence of the expressed protein. When expressed on chicken embryonic fibroblast DF1 cell surface or incorporated onto virus membrane, the signal peptide is cleaved yielding the mature recombinant fusion protein (SEQ ID NO:3) which has a configuration/orientation such that the CD55 SCR is on the outside of the cell or viral membrane, the flexible linker adjacent to the cell or viral membrane should provide maximal flexibility for the SCR of CD55 to exercise its biological function, i.e., disabling C3 convertase which is the central regulator of complement pathway. The flexible linker is followed by a CD8 transmembrane domain and a truncated CD8 intracellular domain.

Example 2

Figure 3:
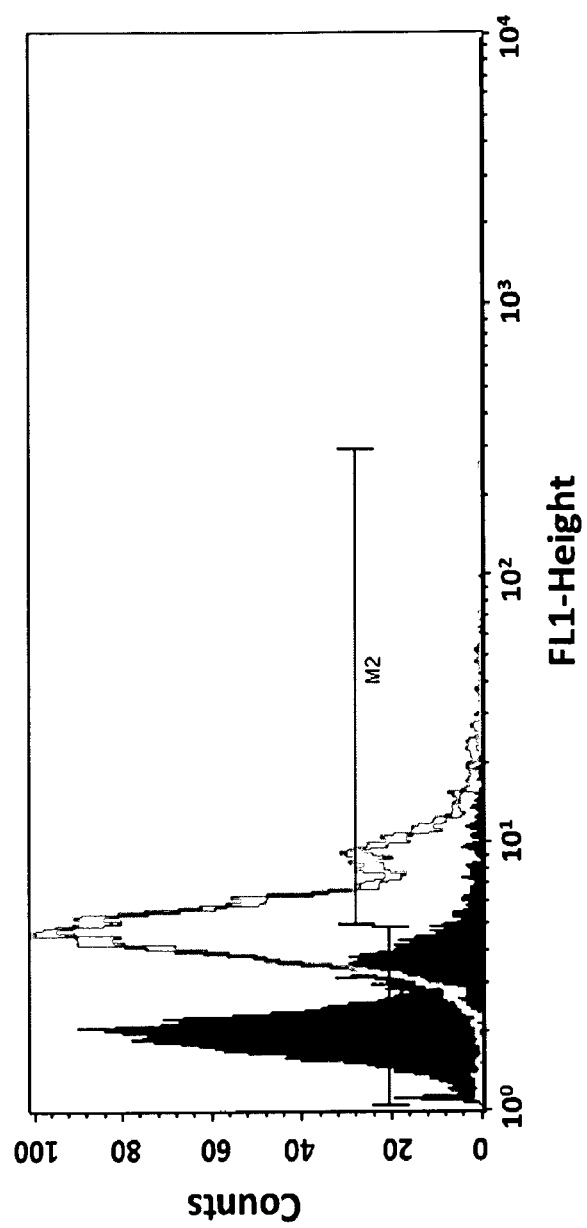

The mammalian expression construct was transfected into chicken embryonic fibroblast DF1 cells via PEI 25K (polyethylenimine, linear 25 kDa, Polysciences, Cat. No. 23966) mediated transfection. Seventy two hours post-transfection, the transfected cells were selected in 300 μg/mL G418 (Geneticin®, aminoglycoside antibiotic) to create a stable cell line that constitutively expresses SEQ ID NO:2. The stable cell line constitutively expressed SEQ ID NO:3 on its cell surface as detected by a monoclonal antibody (R&D Systems, Catalog No. MAB20091) that is specific for mature human CD55. As shown in FIG. 3, the recombinant fusion protein was expressed on the DF1 cells stably transfected with the construct that encodes the recombinant fusion protein as analyzed by flow cytometry (FIG. 3, the histogram on the right). The naïve DF1 cells served as a negative control (FIG. 3, the histogram on the left).

Example 3

The stable cell line expressing SEQ ID NO:3 on the cell surface was infected with wild type NDV that was produced from embryonated chicken eggs. The virus was then titered on human tumor cell line HT1080. Equal amount of virus (measured by PFU) was subjected to incubation with 40% normal human serum (NHS) and 40% heat-inactivated normal human serum (iNHS) respectively. The virus that remained alive after incubation with human serum was then scored on HT1080 cells by plaque assay. The ratio of virus recovered after incubation with NHS vs iNHS was calculated. As shown in Table 1, the recovery rate for the virus produced in embryonated chicken eggs was 0.5%, suggesting vast majority of the NDV particles produced by chicken eggs were inactivated most likely by human alternative complement pathway. Likewise, the recovery rate for the virus produced by the parental chicken embryonic fibroblast DF1 cells was 0.5%. Surprisingly, the recovery rate for the virus produced from the bulk non-clonal DF1 cells that stably expressed SEQ ID NO:3 on the cell surface was 5.8%, greater than 10 fold more than the wild type virus. When a total of 11 clonal populations of DF1 cells expressing SEQ ID NO:3 were examined, the recovery rate ranged from 0.8 to 20% with five clones scoring a lower recovery rate and six clones scoring a higher recovery rate than the bulk non-clonal cell line (Table 1). The virus generated by clone number 8 had a recovery rate of 10% which was 20 fold higher than the virus either produced by embryonated chicken eggs or the parental DF1 cells. The virus generated by clone number 40 had a recovery rate of 20% which was 40 fold higher than the virus either produced by embryonated chicken eggs or the parental DF1 cells. These data strongly suggest that the complement activity presented in normal human serum rapidly destroyed the NDV particles that were produced by embryonated chicken eggs or the parental chicken embryonic fibroblast DF1 cells. However, the new NDV particles produced by DF-1 cells that stably expressed recombinant complement inhibitor on the cell surface showed a remarkable up to 40-fold higher recovery rate as compared to the virus either produced by chicken eggs or the parental DF1 cells after incubation with 40% normal human serum under identical experimental conditions.

TABLE 1

Virus recovery rate measured by the ratio of the virus recovered after incubation with 40% normal human serum (NHS) vs 40% heat-inactivated human serum (iNHS)

| Oncolytic NDV Produced from | % Recovery rate after incubation with human serum |
|---|---|
| Embryonated Chicken Eggs | 0.5 |
| Parental DF1 Cells | 0.5 |
| Non-clonal DF1 cells expressing SEQ ID NO: 3 | 5.8 |
| Clone #1 DF1 expressing SEQ ID NO: 3 | 4.3 |
| Clone #2 DF1 expressing SEQ ID NO: 3 | 5.2 |
| Clone #3 DF1 expressing SEQ ID NO: 3 | 0.8 |
| Clone #4 DF1 expressing SEQ ID NO: 3 | 6.8 |
| Clone #5 DF1 expressing SEQ ID NO: 3 | 3.6 |
| Clone #6 DF1 expressing SEQ ID NO: 3 | 1.5 |
| Clone #7 DF1 expressing SEQ ID NO: 3 | 7.1 |
| Clone #8 DF1 expressing SEQ ID NO: 3 | 10.0 |
| Clone #10 DF1 expressing SEQ ID NO: 3 | 6.1 |
| Clone #11 DF1 expressing SEQ ID NO: 3 | 6.0 |
| Clone #40 DF1 expressing SEQ ID NO: 3 | 20.0 |

Example 4

Figure 4:
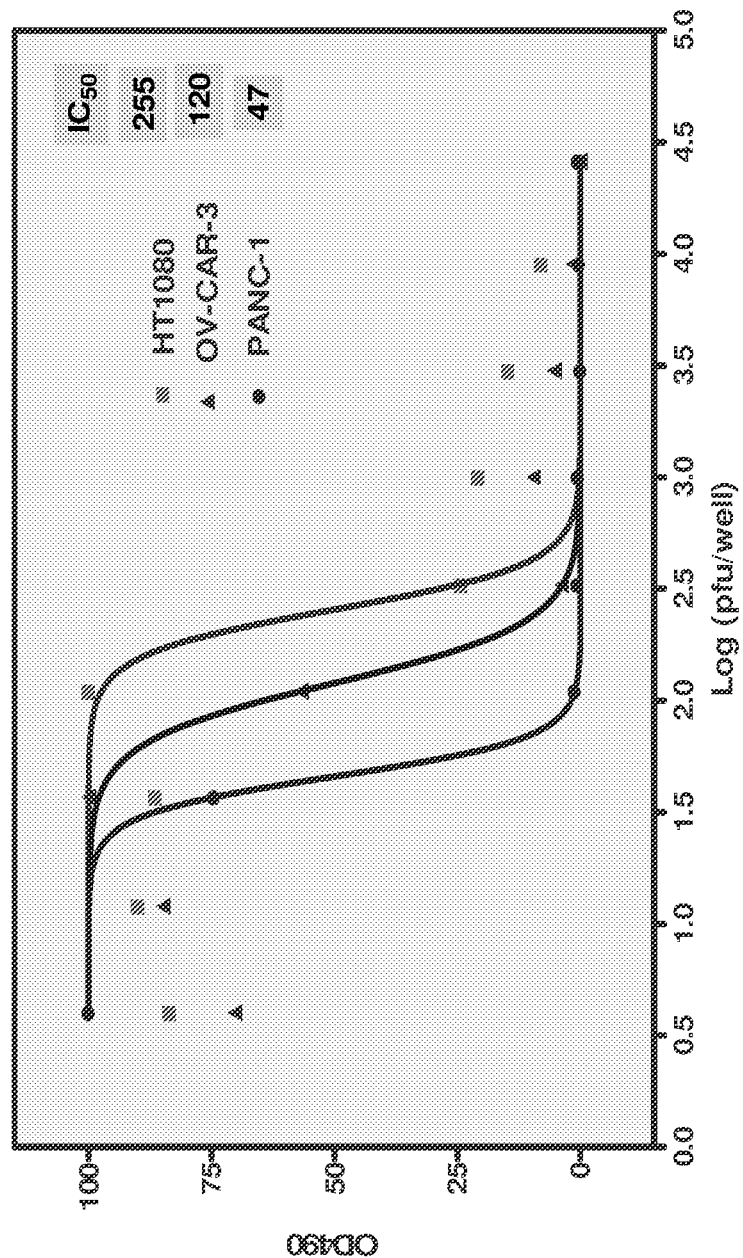

The broad spectrum oncolytic activity of NDV that was produced from the DF1 cells stably expressing the complement inhibitory fusion protein on their cell surface (Clone Number 8) was assessed using CellTiter96® AQueous One Solution. This solution functions similar to MTT (i.e., 3-(4,5-dimethylthiazol-2-yl)-2,5-diphenyltetrazolium bromide) assays where metabolically active cells are able to bio-reduce MTS tetrazolium (i.e., 3-(4,5-dimethylthiazol-2-yl)-5-(3-carboxymethoxyphenyl)-2-(4-sulfophenyl)-2H-tetrazolium) in the reagent into soluble chromogenic formazan. Briefly, three different tumor cell lines HT1080 (fibrosarcoma), PANC-1 (pancreatic epithelial carcinoma) and OV-CARS (ovarian adenocarcinoma) where grown in separate 96 well plates. The following day, serial dilutions of the NDV virus were added to respective wells and the plate was incubated for 6 days at 37° C. incubator with 5% CO2. On Day 6, the absorbance of all wells on each plate was measured at 490 nm using a spectrophotometer. $IC_{50}$ was calculated using 4 parameter logistic nonlinear regression analysis for each cell line. This resulted in final $IC_{50}$ values of 255, 120 and 47 pfu/well for HT1080, OV-CAR-3 and PANC-1 cell lines respectively (FIG. 4). These results indicate that the NDV particles produced by DF-1 cells that stably expressed recombinant complement inhibitor on its cell surface retain the ability to lyse various tumor cell lines in a dose dependent manner.

REFERENCES

Carroll, M. C., E. M. Alicot, P. J. Katzman, L. B. Klickstein, J. A. Smith, and D. T. Fearon. 1988. Organization of the genes encoding complement receptors type 1 and 2, decay-accelerating factor, and C4-binding protein in the RCA locus on human chromosome 1. J. Exp. Med. 167:1271.

Rey-Campos, J., P. Rubinstein, and S. Rodriguez de Cordoba. 1988. A physical map of the human regulator of complement activation gene cluster linking the complement genes CR1, CR2, DAF, and C4BP. J. Exp. Med. 167:664.

Lublin, D. M., and J. P. Atkinson. 1989. Decay-accelerating factor: biochemistry, molecular biology, and function. Annu. Rev. Immunol. 7:35. 5. Nakano, Y., K. Sumida, N. Kikuta, N. H. Miura, T. Tobe, and M. Tomita. 1992. Complete determination of disulfide bonds localized within the short consensus repeat units of decay accelerating factor (CD55 antigen). Biochim. Biophys. Acta 1116:235.

Censullo, P., and M. A. Davitz. 1994a. How GPI-anchored proteins turnover: or where do they go after arrival at the plasma membrane. Semin Immunol. 6:81.

Censullo, P., and M. A. Davitz. 1994b. The fate of GPI-anchored molecules. Braz J. Med. Biol. Res. 27:289

Morgan, B. P., and S. Meri. 1994. Membrane proteins that protect against complement lysis. Springer Semin. Immunopathol. 15:369.

Turner A. J. 1994. PIG-tailed membrane proteins. Essays Biochem. 28:113.

Kim D. D., and W. C. Song. 2006. Membrane complement regulatory proteins. Clin. Immunol. 118:127.

Pecora, A. L., Rizvi, N., Cohen, G. I., Meropol, N. J., Sterman, D., Marshall, J. L., Goldberg, S., Gross, P., O'Neil, J. D., Groene, W. S., Roberts, M. S., Rabin, H., Bamat, M. K., and R. M. Lorence. 2002. Phase I trial of intravenous administration of PV701, an oncolytic virus, in patients with advanced solid cancers. J. Clin. Oncol. 20:2251.

Laurie, S. A., Bell, J. C., Atkins, H. L., Roach, J., Bamat, M. K., O'Neil, J. D., Roberts, M. S., Groene, W. S., and R. M. Lorence. 2006. A phase 1 clinical study of intravenous administration of PV701, an oncolytic virus, using two-step desensitization. Clin. Cancer Res. 12:2555.

Lorence, R. M., Roberts, M. S., O'Neil, J. D., Groene, W. S., Miller, J. A., Mueller, S. N., and M. K. Bamat. 2007. Phase 1 clinical experience using intravenous administration of PV701, an oncolytic Newcastle disease virus. 7:157.

Biswas, M., Johnson, J. B., Kumar, S. R. P., Parks, G. D., and E. Subbiah. 2012. Incorporation of host complement regulatory proteins into Newcastle disease virus enhances complement evasion. J. Virol. 86:12708.

Rangaswamy, U. S., Cotter, C. R., Chang, X., Jin, H., and Z. Chen. 2016. CD55 is a key complement regulatory protein that counteracts complement-mediated inactivation of Newcastle disease virus. J. Gen. Virol. 97:1765.

What is claimed is:

1. A fusion protein comprising: (a) a CD55 peptide sequence comprising four short consensus repeats (SCR) of CD55, (b) a (G4S1)3 linker sequence C-terminal to the CD55 sequence, (c) a CD8 transmembrane domain C-terminal to the linker sequence, and (d) a CD8 intracellular domain C-terminal to the transmembrane domain wherein the CD8 intracellular domain is truncated; and wherein the fusion protein does not contain a GPI anchor.

2. The fusion protein of claim 1, wherein the CD55 peptide sequence is a human CD55 peptide sequence.

3. The fusion protein of claim 1, wherein the fusion protein further comprises a secretory signal peptide N-terminal to sequence (a).

4. The fusion protein of claim 3, wherein the secretory signal peptide is a secretory signal peptide of CD55.

5. The fusion protein of claim 1, having the sequence SEQ ID NO:2.

6. The fusion protein of claim 1, having the sequence SEQ ID NO:3.

7. A nucleic acid encoding the fusion protein of claim 1.

8. The nucleic acid of claim 7, encoding a protein having the sequence SEQ ID NO:2.

9. The nucleic acid of claim 8, having the sequence SEQ ID NO:1.

10. An expression vector comprising the nucleic acid of claim 7, operatively linked to a control sequence.

11. A cell line stably expressing the fusion protein of claim 1 on the cell surface.

12. An enveloped virus incorporating the fusion protein of claim 1 on the virus membrane.

13. The virus of claim 12, wherein the virus is an oncolytic virus.

14. A pharmaceutical composition comprising the virus of claim 13 and a pharmaceutically acceptable carrier.

15. A method for treating a neoplastic condition in a mammalian subject, comprising administering to the subject an amount of the virus of claim 12 eff